United States Patent
Farley

(10) Patent No.: US 10,786,328 B2
(45) Date of Patent: Sep. 29, 2020

(54) ADAPTOR HANDLE FOR SURGICAL RETRACTOR

(71) Applicant: Thompson Surgical Instruments, Inc., Traverse City, MI (US)

(72) Inventor: Dan Farley, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 241 days.

(21) Appl. No.: 15/334,797

(22) Filed: Oct. 26, 2016

(65) Prior Publication Data
US 2018/0110505 A1  Apr. 26, 2018

(51) Int. Cl.
*A61B 90/50* (2016.01)
*A61B 17/02* (2006.01)
*A61B 17/00* (2006.01)

(52) U.S. Cl.
CPC ............ *A61B 90/50* (2016.02); *A61B 17/025* (2013.01); *A61B 2017/0046* (2013.01); *A61B 2017/0069* (2013.01); *A61B 2017/0275* (2013.01)

(58) Field of Classification Search
CPC .... A61B 2017/0256; A61B 2017/0243; A61B 2017/0275; A61B 17/02; A61B 17/025; A61B 17/0218; A61B 17/0293; A61B 90/50
See application file for complete search history.

(56) References Cited

U.S. PATENT DOCUMENTS

| | | | | | |
|---|---|---|---|---|---|
| 2,670,732 | A | * | 3/1954 | Nelson | A61B 90/57 600/234 |
| 3,384,077 | A | * | 5/1968 | Gauthier | A61B 17/0293 600/206 |
| 3,509,873 | A | * | 5/1970 | Karlin | A61B 17/02 600/226 |
| 3,858,578 | A | * | 1/1975 | Milo | A61B 17/02 600/229 |
| 3,910,538 | A | * | 10/1975 | Baitella | F16M 11/14 248/124.1 |
| 4,116,232 | A | * | 9/1978 | Rabban | A61B 17/02 600/196 |
| 4,143,652 | A | * | 3/1979 | Meier | A61B 17/02 600/203 |
| 4,402,481 | A | * | 9/1983 | Sasaki | F16M 11/12 248/282.1 |
| 4,461,284 | A | * | 7/1984 | Fackler | A61B 17/02 248/288.51 |
| 4,467,791 | A | * | 8/1984 | Cabrera | A61B 90/50 248/229.16 |

(Continued)

*Primary Examiner* — Lynnsy M Summitt
(74) *Attorney, Agent, or Firm* — McAndrews, Held & Malloy, Ltd.

(57) ABSTRACT

A surgical retraction system includes a frame and a universal joint coupled to the frame. A handle adaptor secures a surgical retractor to the frame via the universal joint. The handle adaptor includes an extension arm, a hinge, and a clamp. The extension arm comprises an elongated member having a proximal end and a distal end. The elongated member is secured to the frame via the universal joint. The hinge is attached to the distal end of the extension arm. The clamp is attached to the hinge and is configured to receive and retain a handle of a surgical retractor.

20 Claims, 9 Drawing Sheets

(56) References Cited

U.S. PATENT DOCUMENTS

| | | | | |
|---|---|---|---|---|
| 4,606,522 A * | 8/1986 | Heifetz | F16C 11/06 | 248/276.1 |
| 4,616,635 A * | 10/1986 | Caspar | A61B 17/02 | 600/215 |
| 4,653,481 A * | 3/1987 | Howland | A61B 17/7001 | 248/67.5 |
| 4,934,352 A * | 6/1990 | Sullivan, Jr. | A61B 17/02 | 600/213 |
| 4,971,037 A * | 11/1990 | Pelta | A61B 17/0206 | 403/390 |
| 5,035,232 A * | 7/1991 | Lutze | A61B 17/02 | 600/213 |
| 5,303,694 A | 4/1994 | Mikhail | | |
| 5,320,444 A * | 6/1994 | Bookwalter | A61B 17/6408 | 248/231.41 |
| 5,365,921 A * | 11/1994 | Bookwalter | A61B 17/0206 | 269/261 |
| 5,375,481 A * | 12/1994 | Cabrera | A61B 17/0293 | 248/316.4 |
| 5,380,331 A * | 1/1995 | Mikhail | A61B 17/02 | 606/53 |
| D369,860 S * | 5/1996 | Koros | D24/133 | |
| 5,513,827 A * | 5/1996 | Michelson | A61B 17/02 | 248/160 |
| 5,520,610 A * | 5/1996 | Giglio | A61B 17/0293 | 600/208 |
| 5,609,565 A * | 3/1997 | Nakamura | A61B 90/50 | 248/278.1 |
| 5,738,685 A * | 4/1998 | Halm | A61B 17/7001 | 411/308 |
| 5,746,743 A * | 5/1998 | Greenberg | A61B 17/02 | 600/210 |
| 5,772,583 A * | 6/1998 | Wright | A61B 17/0206 | 403/389 |
| 5,846,191 A * | 12/1998 | Wells | A61B 1/32 | 600/201 |
| 5,902,233 A * | 5/1999 | Farley | A61B 17/0206 | 600/213 |
| 5,918,844 A * | 7/1999 | Ognier | F16M 11/14 | 248/276.1 |
| 5,967,973 A * | 10/1999 | Sherts | A61B 17/0293 | 600/205 |
| 5,984,865 A * | 11/1999 | Farley | A61B 17/02 | 600/213 |
| 5,984,867 A * | 11/1999 | Deckman | A61B 17/0206 | 600/231 |
| 6,083,154 A * | 7/2000 | Liu | A61B 17/0293 | 600/231 |
| 6,085,749 A * | 7/2000 | Wardle | A61B 90/50 | 128/845 |
| 6,132,370 A * | 10/2000 | Furnish | A61B 17/0206 | 600/215 |
| 6,254,535 B1 * | 7/2001 | Furnish | A61B 17/0206 | 600/213 |
| 6,315,718 B1 * | 11/2001 | Sharratt | A61B 17/02 | 600/228 |
| 6,322,500 B1 * | 11/2001 | Sikora | A61B 17/0206 | 600/219 |
| 6,338,738 B1 * | 1/2002 | Bellotti | A61B 17/0206 | 600/201 |
| 6,340,345 B1 * | 1/2002 | Lees | A61B 17/0206 | 600/226 |
| 6,368,271 B1 * | 4/2002 | Sharratt | A61B 17/025 | 600/228 |
| 6,572,540 B2 * | 6/2003 | Dobrovolny | A61B 17/02 | 600/226 |
| 6,673,073 B1 * | 1/2004 | Schafer | A61B 17/7049 | 606/250 |
| 6,808,493 B1 * | 10/2004 | Bookwalter | A61B 17/02 | 600/231 |
| 6,860,877 B1 * | 3/2005 | Sanchez | A61B 17/12 | 600/229 |
| 7,118,571 B2 * | 10/2006 | Kumar | A61B 17/7032 | 606/278 |
| 7,537,565 B2 * | 5/2009 | Bass | A61B 17/0206 | 600/219 |
| 7,753,844 B2 * | 7/2010 | Sharratt | A61B 17/0206 | 600/201 |
| 8,216,133 B2 * | 7/2012 | Chappuis | A61B 8/06 | 600/202 |
| RE43,806 E * | 11/2012 | Carnevali | F16M 11/14 | 248/181.1 |
| 8,623,022 B2 * | 1/2014 | Forton | A61B 17/708 | 606/104 |
| 8,900,137 B1 * | 12/2014 | Lovell | A61B 17/02 | 600/210 |
| 9,179,945 B2 * | 11/2015 | Hsueh | A61B 17/7074 | |
| 9,237,933 B2 * | 1/2016 | Agbodoe | F16M 11/40 | |
| 9,636,097 B2 * | 5/2017 | Bass | A61B 17/0206 | |
| 9,848,862 B2 * | 12/2017 | Bass | A61B 17/02 | |
| 9,872,675 B2 * | 1/2018 | Nowak | A61B 17/0206 | |
| 9,918,795 B2 * | 3/2018 | Wyslucha | A61B 90/50 | |
| 2001/0020121 A1 * | 9/2001 | Hu | A61B 17/02 | 600/232 |
| 2001/0025136 A1 * | 9/2001 | Leonard | A61B 17/00234 | 600/210 |
| 2001/0034473 A1 * | 10/2001 | Cartier | A61B 1/32 | 600/229 |
| 2002/0058856 A1 * | 5/2002 | Peng | A61B 17/02 | 600/37 |
| 2002/0161446 A1 * | 10/2002 | Bryan | A61B 17/02 | 623/17.15 |
| 2003/0139651 A1 * | 7/2003 | Holland | A61B 17/00008 | 600/245 |
| 2003/0191372 A1 * | 10/2003 | Dobrovolny | A61B 17/02 | 600/226 |
| 2003/0220547 A1 * | 11/2003 | Holland | A61B 17/00008 | 600/245 |
| 2004/0127773 A1 * | 7/2004 | Douglas | A61B 17/02 | 600/227 |
| 2004/0129109 A1 * | 7/2004 | Phillips | A61B 17/02 | 74/577 M |
| 2004/0147812 A1 * | 7/2004 | Hamel | A61B 1/32 | 600/213 |
| 2004/0193018 A1 * | 9/2004 | Thalgott | A61B 17/02 | 600/227 |
| 2004/0199055 A1 * | 10/2004 | Mulac | A61B 17/02 | 600/226 |
| 2004/0230191 A1 * | 11/2004 | Frey | A61B 17/0293 | 606/57 |
| 2004/0242968 A1 * | 12/2004 | Hill | A61B 17/02 | 600/210 |
| 2005/0020885 A1 * | 1/2005 | Rein | A61B 17/02 | 600/228 |
| 2005/0043717 A1 * | 2/2005 | Snow | A61B 17/02 | 606/1 |
| 2005/0119697 A1 | 6/2005 | Sharratt | | |
| 2006/0063977 A1 * | 3/2006 | Sharratt | A61B 17/02 | 600/212 |
| 2007/0066872 A1 | 3/2007 | Morrison et al. | | |
| 2007/0093696 A1 * | 4/2007 | Sharratt | A61B 17/02 | 600/235 |
| 2007/0213597 A1 * | 9/2007 | Wooster | A61B 17/02 | 600/234 |
| 2007/0282311 A1 * | 12/2007 | Scott | A61B 17/02 | 606/1 |
| 2008/0071145 A1 * | 3/2008 | Bjork | A61B 17/02 | 600/227 |
| 2008/0076968 A1 * | 3/2008 | Bollier | A61B 17/02 | 600/227 |
| 2008/0161650 A1 * | 7/2008 | Hestad | A61B 17/02 | 600/245 |
| 2008/0221586 A1 * | 9/2008 | Garcia-Bengochea | A61B 17/02 | 606/108 |
| 2009/0012370 A1 | 1/2009 | Gutierrez et al. | | |
| 2009/0204148 A1 * | 8/2009 | Lenke | A61B 17/02 | 606/246 |

(56) References Cited

U.S. PATENT DOCUMENTS

| | | | | |
|---|---|---|---|---|
| 2009/0264710 A1* | 10/2009 | Chana | A61B 17/02 | 600/233 |
| 2010/0081886 A1* | 4/2010 | Komuro | A61B 1/00149 | 600/229 |
| 2010/0113885 A1* | 5/2010 | McBride | A61B 1/32 | 600/224 |
| 2010/0217089 A1* | 8/2010 | Farley | A61B 17/02 | 600/213 |
| 2010/0256454 A1* | 10/2010 | Farley | A61B 17/02 | 600/210 |
| 2011/0137130 A1* | 6/2011 | Thalgott | A61B 17/0206 | 600/232 |
| 2011/0270042 A1* | 11/2011 | Giulianotti | A61B 17/02 | 600/228 |
| 2012/0238828 A1* | 9/2012 | Fricke | A61B 17/02 | 600/230 |
| 2012/0298820 A1* | 11/2012 | Manolidis | A61B 17/02 | 248/222.14 |
| 2013/0066162 A1* | 3/2013 | Schulte | A61B 17/02 | 600/210 |
| 2013/0245383 A1* | 9/2013 | Friedrich | A61B 17/02 | 600/228 |
| 2014/0039267 A1* | 2/2014 | Seex | A61B 17/3403 | 600/206 |
| 2015/0087918 A1* | 3/2015 | Vasan | A61B 13/00 | 600/213 |
| 2015/0157306 A1* | 6/2015 | Schuele | A61B 17/02 | 600/227 |
| 2015/0282795 A1* | 10/2015 | Schabert | A61B 17/0218 | 600/213 |
| 2016/0242757 A1* | 8/2016 | Cryder | A61B 17/0206 | |
| 2016/0287234 A1* | 10/2016 | Bass | A61B 17/02 | |
| 2017/0042527 A1* | 2/2017 | Farley | A61B 17/02 | |
| 2018/0021033 A1* | 1/2018 | Friedrich | A61B 17/02 | |

* cited by examiner

ADAPTOR HANDLE FOR SURGICAL RETRACTOR

TECHNICAL FIELD

The invention relates to a surgical retraction systems, and more particularly to securing surgical retractors to a retractor frame.

BACKGROUND

Surgical retraction systems may be used during surgical procedures to access internal organs and bone structures (e.g., a hip joint). Such retraction systems may include surgical retractors that retract soft tissue of the patient. Retractors may be hand held or attached to a surgical retraction frame. Some retractors operate as levers. For example, a distal end of the retractor may pass through an incision in the patient, and the distal end may be placed behind a bone structure. Then, by levering a handle at a proximal end of the retractor, the retractor may retract the soft tissue and hold the incision open in order for a surgeon to access organs and other biological structures via the incision.

SUMMARY

Various aspects of this disclosure are directed to adaptor handles and surgical retraction systems having adaptor handles that secure surgical retractors to a frame of the surgical retraction system. For example and without limitation, various aspects of this disclosure describe a universal adaptor handle suitable for securing different types of surgical retractors to a surgical retraction system frame. Various other aspects of this disclosure provide an adaptor handle that secures a surgical retractor to a surgical retraction system frame in an adjustable manner.

DETAILED DESCRIPTION OF THE INVENTION

Figure 1:
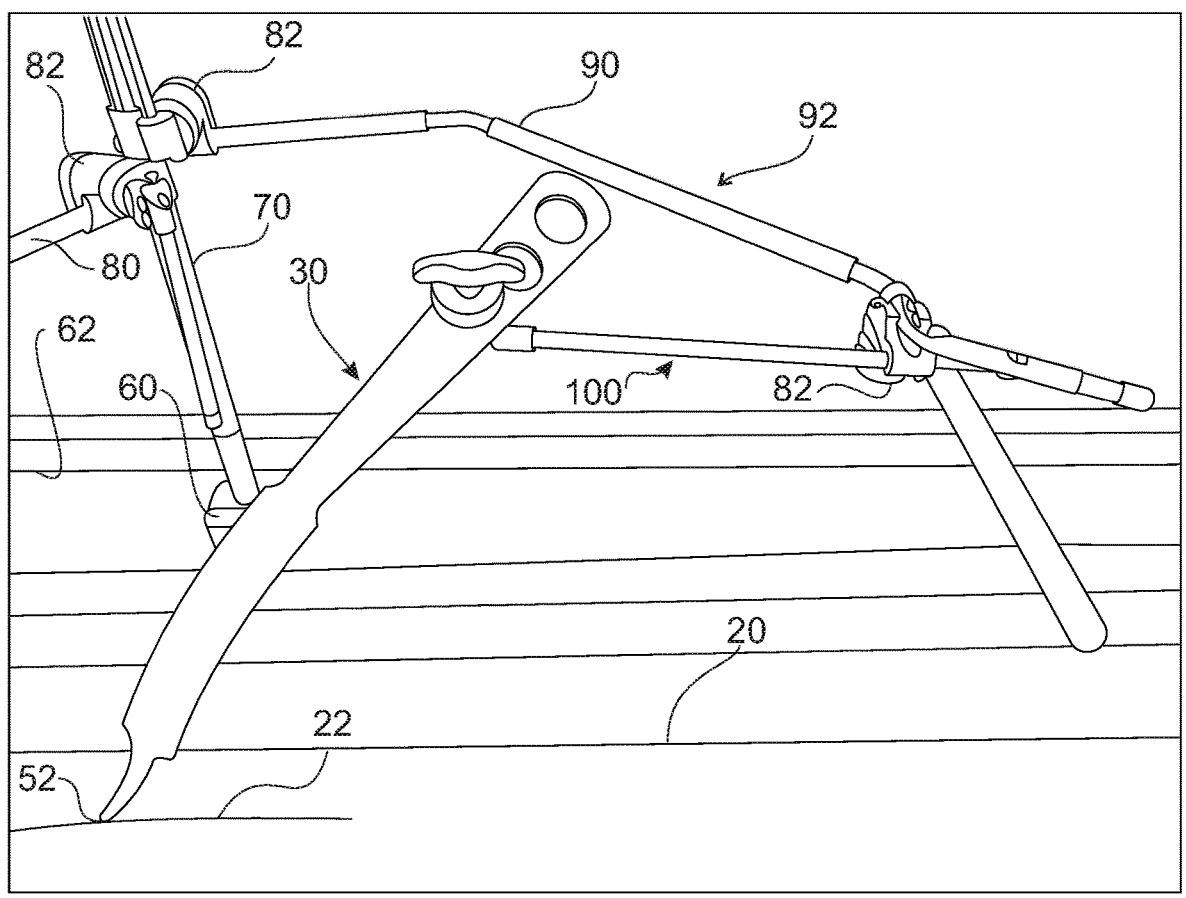
FIG. 1 shows an embodiment of a surgical retraction system that may be used to open an incision such as an incision along the incision line of FIG. 1.

The following discussion presents various aspects of the present disclosure by way of one or more examples. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure. Similarly, various spatial terms, such as "upper," "lower," "side," and the like, may be used in distinguishing one element from another element in a relative manner. It should be understood, however, that components may be oriented in different manners, for example a component may be turned sideways so that its "top" surface is facing horizontally and its "side" surface is facing vertically, without departing from the teachings of the present disclosure.

In the drawings, various dimensions (e.g., layer thickness, width, etc.) may be exaggerated for illustrative clarity. Additionally, like reference numbers are utilized to refer to like elements through the discussions of various examples.

The discussion will now refer to various example illustrations provided to enhance the understanding of the various aspects of the present disclosure. It should be understood that the scope of this disclosure is not limited by the specific characteristics of the examples provided and discussed herein.

A surgical retraction system 10 is shown in FIG. 1. The surgical retraction system 10 may be used to retract body tissue of a patient 20 along an incision 22 to assist the surgeon in accessing internal organs, bone structures, or other internal structures of the patient 20. To this end, the retraction system 10 may include one or more surgical retractors 30 that each have a handle 40 and a blade 50. A distal end 52 of the retractor blade 50 may be placed through the incision 22. The distal end 52 may be further placed under a bone structure of the patient 20. After such placement, the handle 40 extending from a proximal end 54 of the blade 50 may be levered in a downward direction to cause the retractor 30 to pivot about the distal end 52, which is engaged with the bone structure of the patient 20. Such pivoting may cause lateral movement of the retractor blade 50 away from the incision 22 and retract body tissue away from the incision 22 in the process.

As depicted, the retraction system 10 may include one or more rail clamps 60. Each rail clamp 60 may be secured to a horizontal rail 62 located on each side of a conventional operating table. A post 70 may extend vertically from a secured rail clamp 60 to provide support for a cross bar 80. The cross bar 80 may be secured to one of the posts 70 by a universal joint clamp 82. In addition, one or more lateral arms 90 may be secured to post 70 via another universal clamp 82. The cross bar 80 and the one or more lateral arms 90 generally define a frame 92 to which retractors 30 may be secured.

FIG. 1 depicts a single retractor 30 secured to lateral arm 90 of the retraction frame 92 via a universal clamp 82 and handle adaptor 100. However, any number of retractors 30 may be secured along the cross bar 80 via a corresponding number of universal clamps 82 and handle adaptors 100. Similarly, any number of retractors 30 may be secured to one of the lateral arms 90 via a corresponding number of universal clamps 82 and handle adaptors 100.

Figure 2:
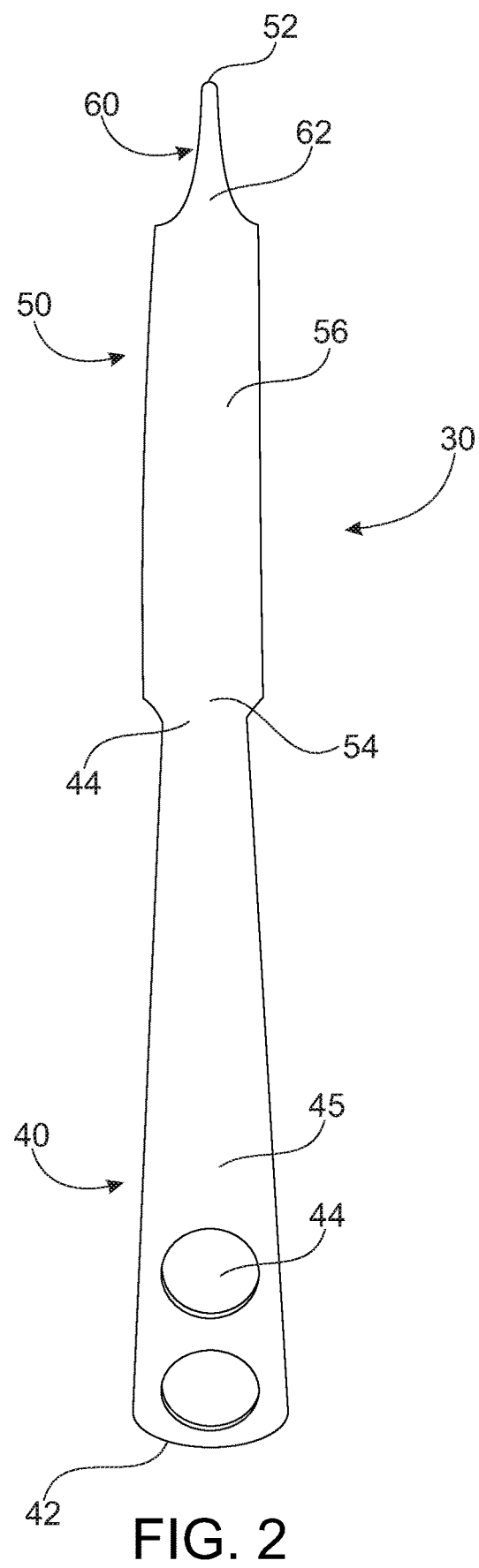
FIG. 2 depicts a top view of a first type of a surgical retractor shown in the surgical retraction system of FIG. 1.
Figure 3:
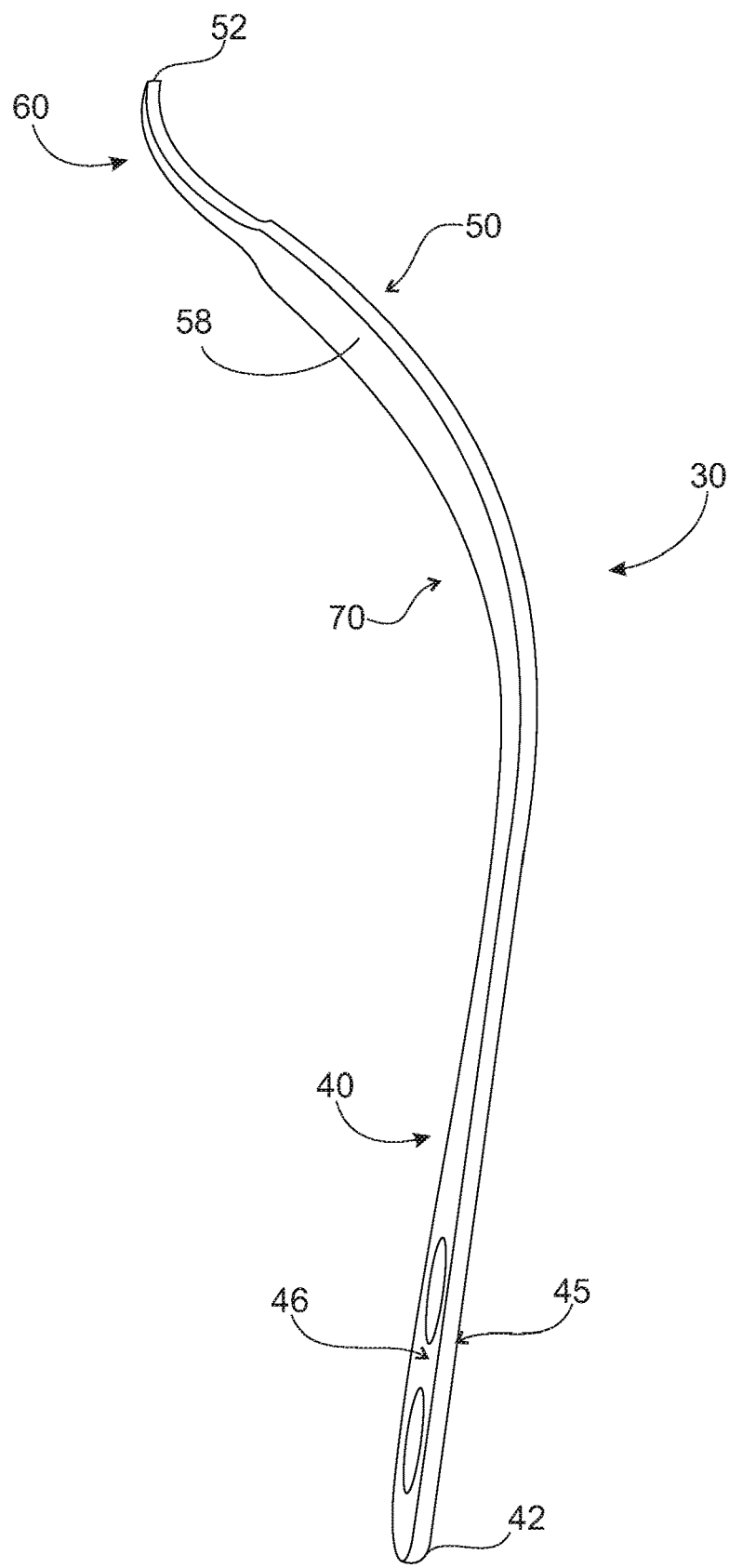
FIG. 3 depicts a side view of the first type of a surgical retractor shown in FIG. 2.

Referring now to FIGS. 2 and 3, further details of the surgical retractor 30 are shown. As shown, the retractor 30 may include the blade 50 and the handle 40 attached to a proximal end 54 of the blade. In the depicted embodiment, the retractor 30 may have a single-piece construction in which the handle 40 and blade 50 are integrally formed from surgical-grade stainless steel. However, the retractor 30 in other embodiments may utilize other surgically-safe materials and/or may have a multi-piece construction. For example, the handle 40 may be implemented as a separate piece that is welded or otherwise affixed to the blade 50. In some embodiments, the handle 40 may be detachably secured to the blade 50.

As shown, the blade 50 may comprise a blade body 56 having a proximal end 54 to which the handle 40 is attached and a distal end 52 to be inserted into the patient 20. The blade body 56 and distal end 52 are configured to contact a patient. In particular, as noted above, the distal end 52 may engage a bone structure or another internal, anatomical feature of the patient 20. The blade body 56 may provide a bottom surface 58 configured to engage and retract anatomy tissue proximate incision 22.

In the embodiment depicted, the proximal end 54 of the blade 50 is integrally attached to the handle 40. In other embodiments, the handle 40 may be a separate component that has been permanently attached to the proximal end 54 of the blade 50. In yet other embodiments, the proximal end 54 may include a connector (not shown) such as, for example, a connection nipple. The connection nipple may permit detachably securing the handle 40 to the proximal end 54 of the blade 50.

The blade body 56 may include a lower blade portion 60 and an upper blade portion 70. The lower blade portion 60 may be hook-shaped, which aids in engaging and/or securing the distal end 52 of the blade 50 to a bone structure or other internal structure of the patient 20. In particular, the lower blade portion 60 may be curved upwardly and the distal end 52 may be pointed such that the distal end 52 and an upper surface 62 of the lower blade portion 60 may engage and hook under a bone structure or other internal structure of the patient 20.

The upper blade portion 70 may be curved downwardly. Thus, the upper blade portion 70 is curved in the opposite direction as the lower blade portion 60. Such opposite curvature of the lower and upper blade portions 60, 70 results in the blade body 56 have a generally S-shaped side profile as best shown in FIG. 3. Such curvature generally provides the retraction capabilities of the retractor 30. Namely, the distal end 52 may engage and hook under a bone structure or other internal structure of the patient 20, thus creating a generally stationary pivot point about which the retractor 30 may rotate. In such an engagement, pushing downward upon handle 40 causes the retractor 30 to rotate about the pivot point causing the bottom surface 58 of the upper blade portion 70 to engage and retract soft tissue away from distal end 52 and the incision 22.

As shown, the handle 40 may include a proximal end 42 and a distal end 44. The distal end 44 may be attached to the proximal end 54 of the blade 50 as discussed above. The proximal end 52 may be configured in a manner that permits attaching or otherwise securing the retractor 30 to the frame of the retraction system 10. To this end, the proximal end 42 may include one or more holes 44 that pass between a top surface 45 and a bottom surface 46 of the handle 40. A screw or other type of fastener may pass through such holes 44 to secure the handle 40 of the retractor 30 directly to the frame of the retraction system 10 or to secure the handle 40 to the frame of the retraction system 10 via an adapter or other connector.

Figure 4:
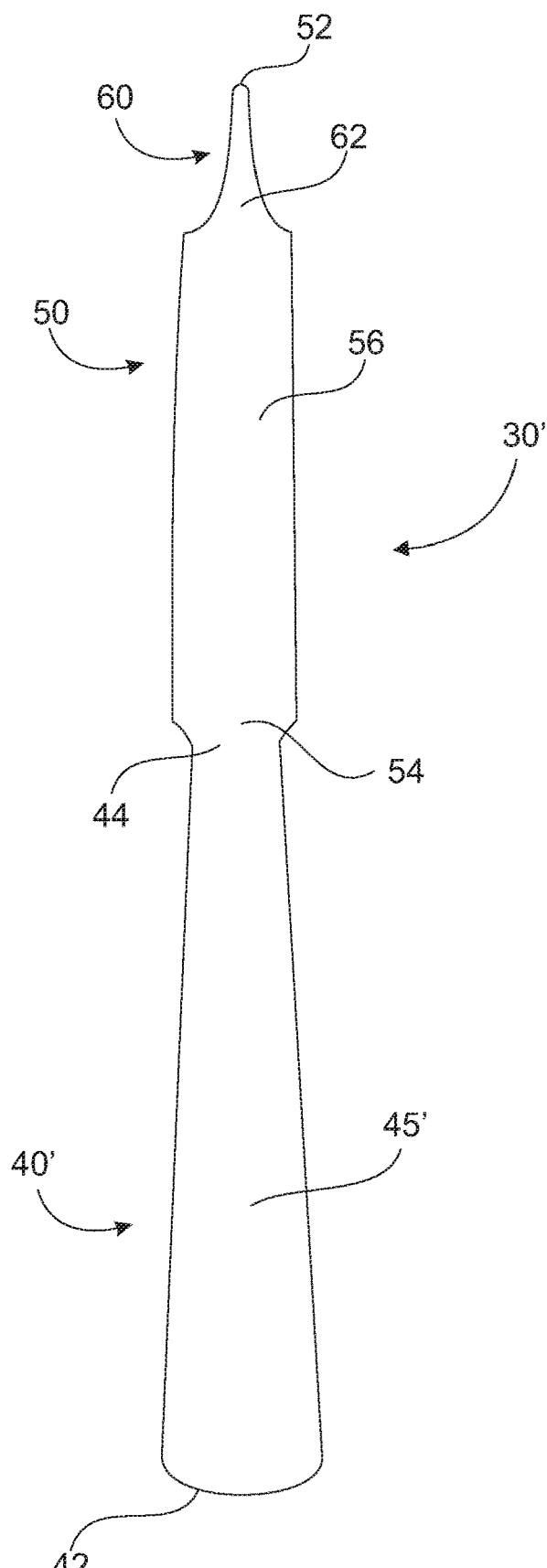
FIG. 4 depicts a top view of a second type of a surgical retractor that may be used with the surgical retraction system of FIG. 1.
Figure 5:
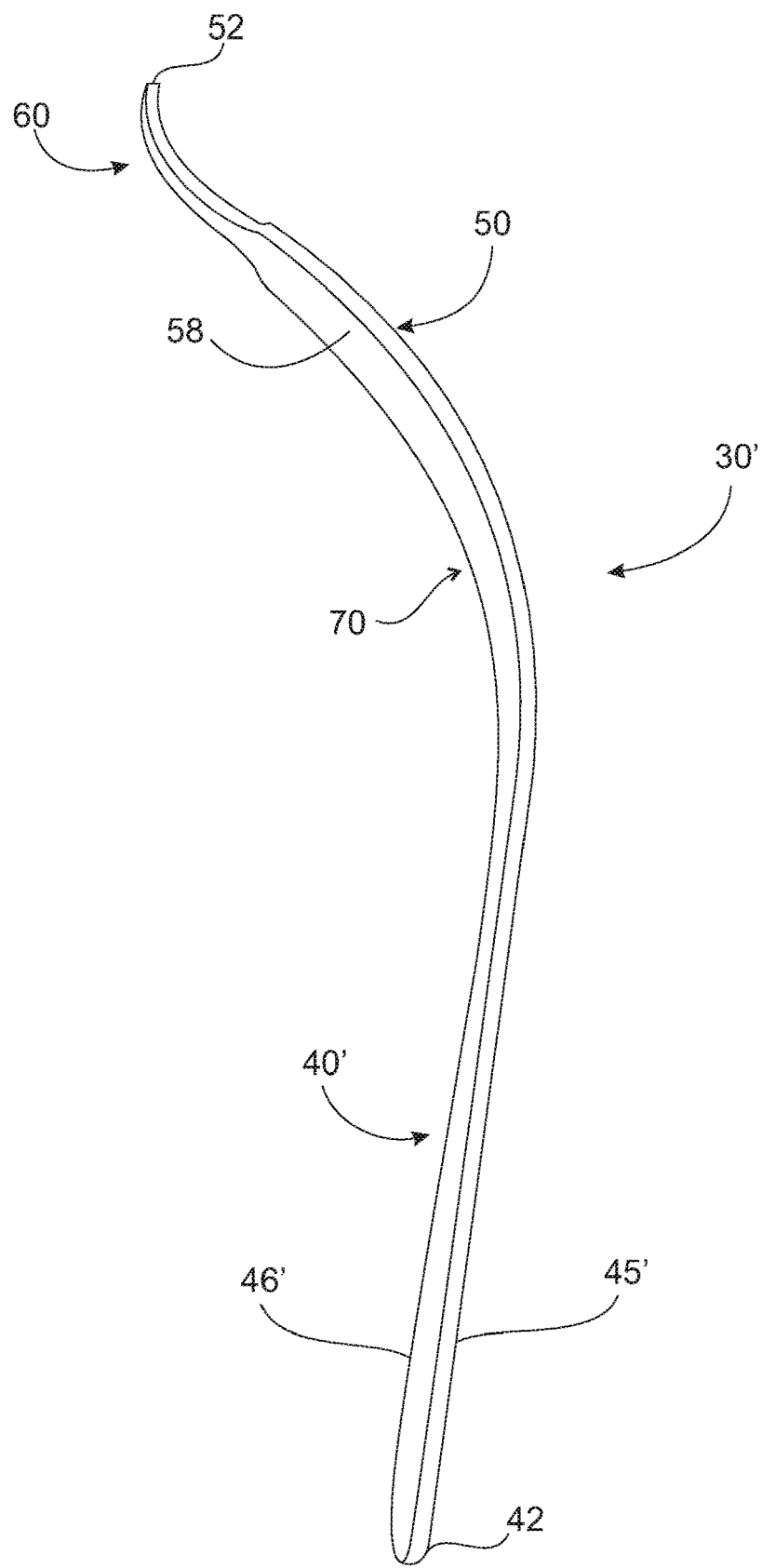
FIG. 5 depicts a side view of the second type of a surgical retractor shown in FIG. 4.

Referring now to FIGS. 4 and 5, details of another embodiment of a surgical retractor 30' are shown. As shown, the retractor 30' of FIGS. 4 and 5 may be implemented in a manner similar to the retractor 30 of FIGS. 2 and 3. The retractor 30', however, does not include holes 44 in its handle 40'. Instead, the retractor handle 40' may provide a smooth, top surface 45' and a smooth, bottom surface 46'. As such, the retractor 30' may be secured to the frame of the retraction system 10 using fasteners that do not pass through the retractor 30'. For example, the retractor 30' may be secured to the frame using rubber bands, ties, threads, which may be wrapped around the handle 40'.

In view of FIGS. 2-5, the surgical retraction system 10 may utilize retractors 30, 30' that are secured to the frame via different manners. For example, retractor 30 may be secured via the use of screws passing through holes 44 whereas retractor 30' may be secured via bands wrapped around handle 40'. Moreover, directly securing retractors 30, 30' to the frame via screws, bands, or other fasteners is fairly restrictive and makes it difficult to properly place the retractor 30, 30' in the incision 22 while at the same time sufficiently securing the retractor 30, 30' to the frame such that the retractor 30, 30' does not shift during a surgical procedure.

Referring now to FIGS. 6-9, the handle adaptor 100 of FIG. 1 is depicted in greater detail. The handle adaptor 100 may be used to secure different types of retractors such as, for example, retractors 30, 30' to the surgical retention system frame. Moreover, due to its adjustment capabilities, the handle adaptor 100 may ease the process of securing such retractors 30, 30' to the frame.

Figure 6:
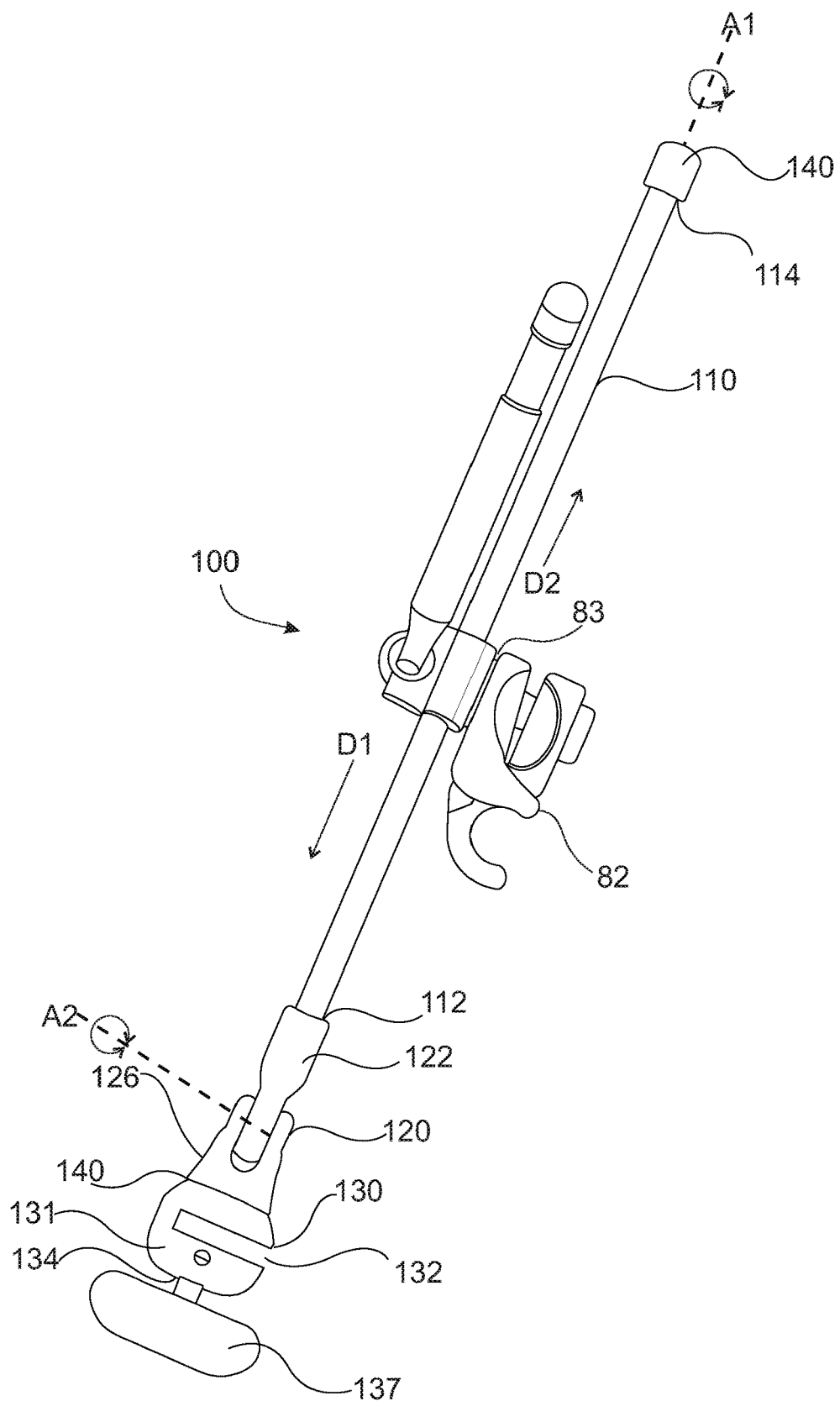
FIG. 6 depicts a perspective view of a handle adaptor coupled to a universal joint of the retraction system of FIG. 1.

As shown, the handle adaptor 100 may include an extension arm 110, a hinge 120, a swivel clamp 130, and a stop 140. As depicted in FIG. 6, the extension arm 110 may comprise an elongated member having a distal end 112 and a proximal end 114. In the depicted embodiment, the elongated member forming the extension arm 110 may be rod-shaped with a circular cross section though other shapes and cross sections are contemplated.

As shown, the extension arm 110 may pass through a clamp 83 of a universal joint 82 that is used to secure the handle adaptor 100 to the surgical retraction system frame. The clamp 83 may be loosened or disengaged to permit the extension arm 100 to slide and/or rotate with respect to the clamp 83. In particular, when the clamp 83 is disengaged, the extension arm 110 may be pulled away from the clamp 83 in direction D1 to extend a distal end 112 of the arm 110 further from the frame. Furthermore, the extension arm 110 may be pushed toward the clamp 83 in direction D2 to retract the distal end 112 of the arm 110 closer to the frame.

As noted above, the extension arm 110 may have a circular, cross-section. The clamp 83 may likewise have a circular, cross-section. The cross-sections of the extension arm 110 and clamp 83 may permit the extension arm 110 to be rotated freely about axis A1. Such rotation may be used to adjust an orientation of a pivot axis A2 provided by the hinge 120. The extension arm 100 and/or clamp 83 in other embodiments may have non-circular, cross-sections, which permit limited rotation of extension arm 100 about axis A1. For example, an octagonal cross-section may provide eight distinct orientations of the extension arm 110 with respect to the clamp 8 about axis A1.

Thus, while the clamp 83 is disengaged, the orientation of the extension arm 110 with respect to the clamp 83 may be adjusted. Conversely, when the clamp 83 is engaged, the clamp 83 may prevent further extending, retracting, and/or rotating of the extension arm 110. Suitable embodiments of universal joints or clamps for universal joint 82 are described in detail in U.S. Pat. Nos. 5,897,087 and 6,033,363, which are incorporated herein by reference.

As shown, the stop 140 may be affixed to a proximal end 114 of the extension arm 110. The stop 140 is generally configured to prevent the extension arm 110 from being inadvertently pulled too far from a disengaged, clamp 83 as the extension arm 110 is extended from the clamp 83. To this end, the stop 140 may have a greater outer circumference than an outer circumference of the extension arm 110 and an inner circumference of the disengaged, clamp 83.

The hinge 120 may be affixed to the distal end 112 of the extension arm 110. In particular, the hinge 120 may comprise a first leaf 122 providing a barrel 124 and a second leaf 126 providing a pin 128. The first leaf 122 may be affixed to the distal end 112 of the extension arm 110 such that the barrel 124 projects from the distal end 112. In one embodiment, the first leaf 122 has an outer circumference that is greater than the outer circumference of the extension arm 110 and the inner circumference of the disengaged, clamp 83. In this manner, the first leaf 122 may function as another stop that prevents the extension arm 110 from being inadvertently pushed too far into the disengaged, clamp 83 as the extension arm 110 is retracted toward the clamp 83.

The pin 128 of the second leaf 126 may pass through the barrel 124 of the first leaf 122. The pin 128 and barrel 124 may cooperate to provide a pivot point that permits the second leaf 126 to rotate about an axis A2 that extends longitudinally along the pin 128 and barrel 124. In this manner, the first and second leaves 122, 126 may form the hinge 120 that permits movement of the clamp 130 in relation to the extension arm 110 about the axis A2. In the depicted embodiment, the first leaf 122 provides the barrel 124 of the hinge 120 and the second leaf 126 provides the pin 128 of the hinge 120. However, in other embodiments, the first leaf 122 may provide the pin 128 and the second leaf 126 may provide the barrel 124.

As shown, the handle adapter 100 further includes the clamp 130. The clamp 130 is generally configured to receive and secure the handle 40, 40' of a retractor 30, 30' to the frame via hinge 120 and extension arm 110. To this end, the clamp 130 may include a clamp body 131 having a slot 132 configured to receive a handle 40, 40' of a retractor 30, 30' and a screw 135 configured to engage a surface of the handle 40, 40'. In particular, the slot 132 of the clamp body 131 may be defined by an proximal surface 133 and a distal surface 134 that respectively align with an upper surface and lower surface of the handle 40, 40' when such a handle is inserted into the slot 132. The screw 135 may extend through a distal end 138 of the clamp body 131 such that the screw 135 passes through the proximal surface 133 of the slot 132. Tightening the screw 135 may cause a tip 136 of the screw 135 to advance into the slot 132, engage an upper surface of the handle 40, 40', and clamp the handle 40, 40' between the tip 136 and the distal surface 134 of the slot 132.

As shown, the screw 135 may include an enlarged head or knob 137 opposite its tip 136, which may permit hand tightening and loosening of the screw 135. As such, the handle 40, 40' may be secured in the clamp 130 without the need of an external tool such as a screwdriver or wrench.

Figure 7:
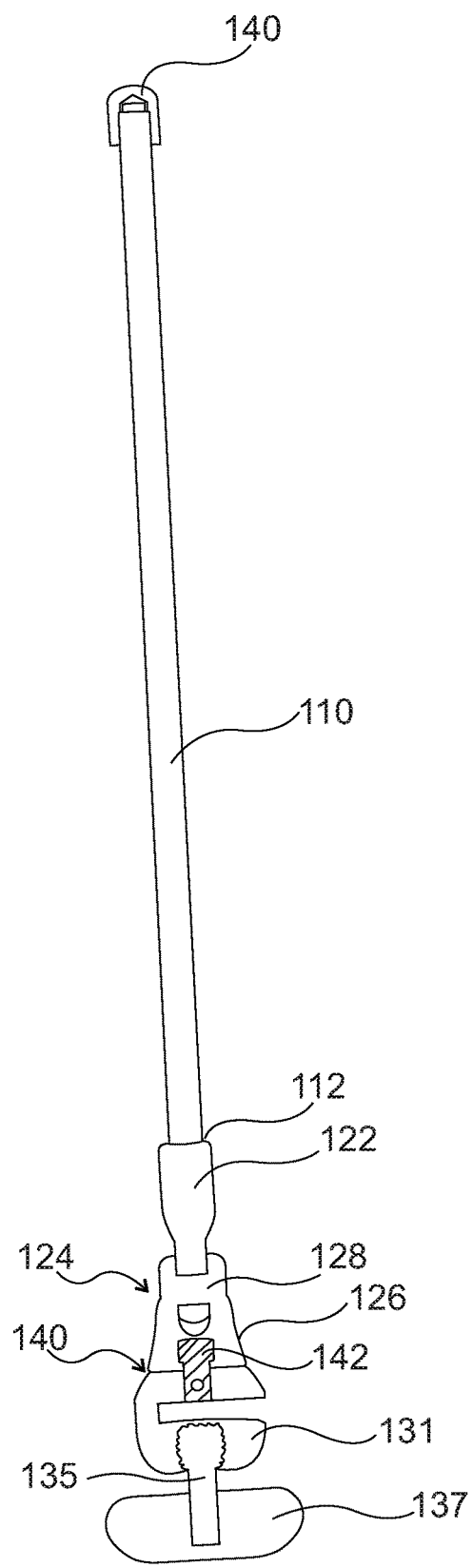
FIG. 7 depicts a first cross-section of the handle adaptor shown in FIG. 6.
Figure 8:
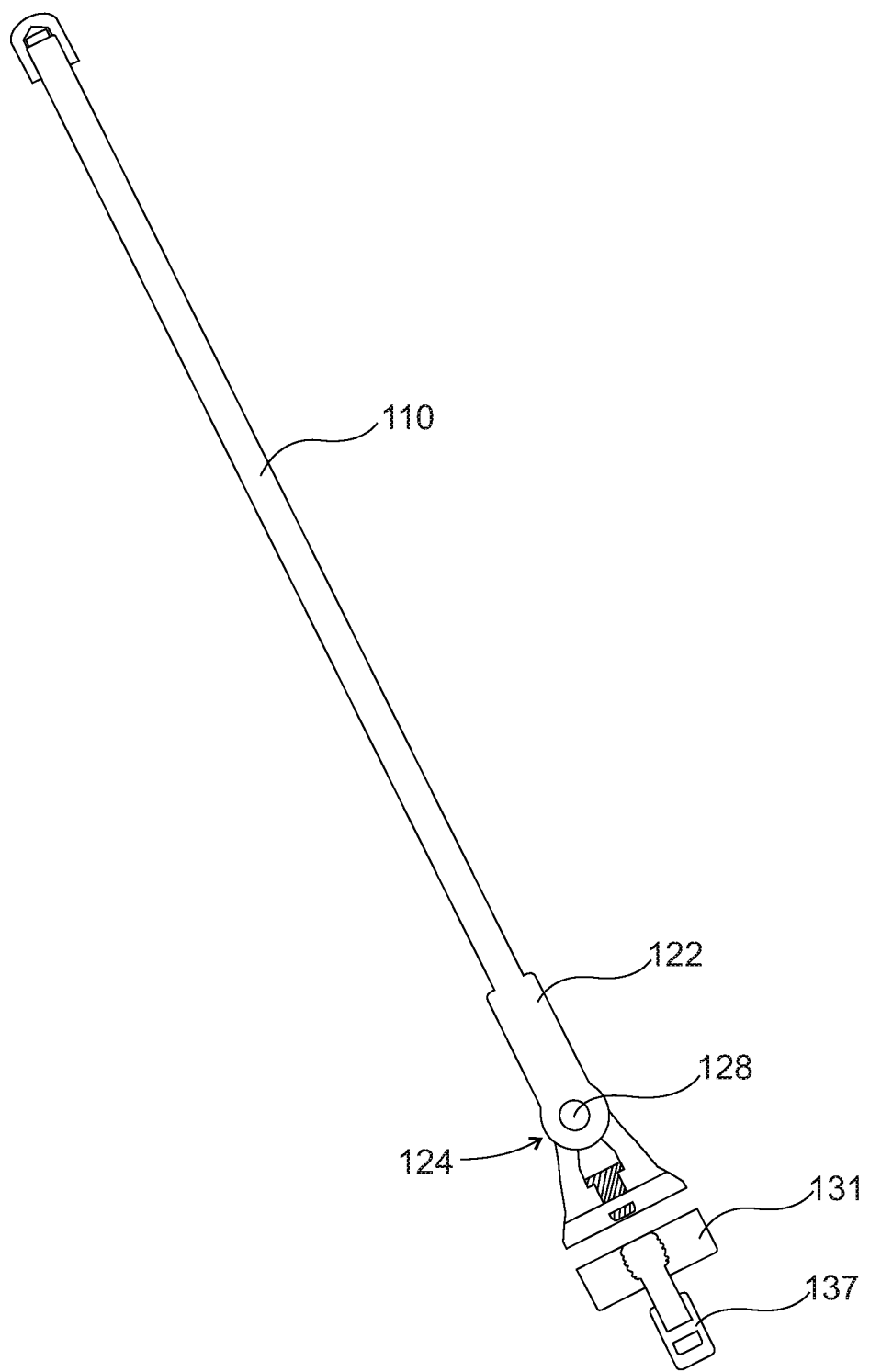
FIG. 8 depicts a second cross-section of the handle adaptor shown in FIG. 6.
Figure 9:
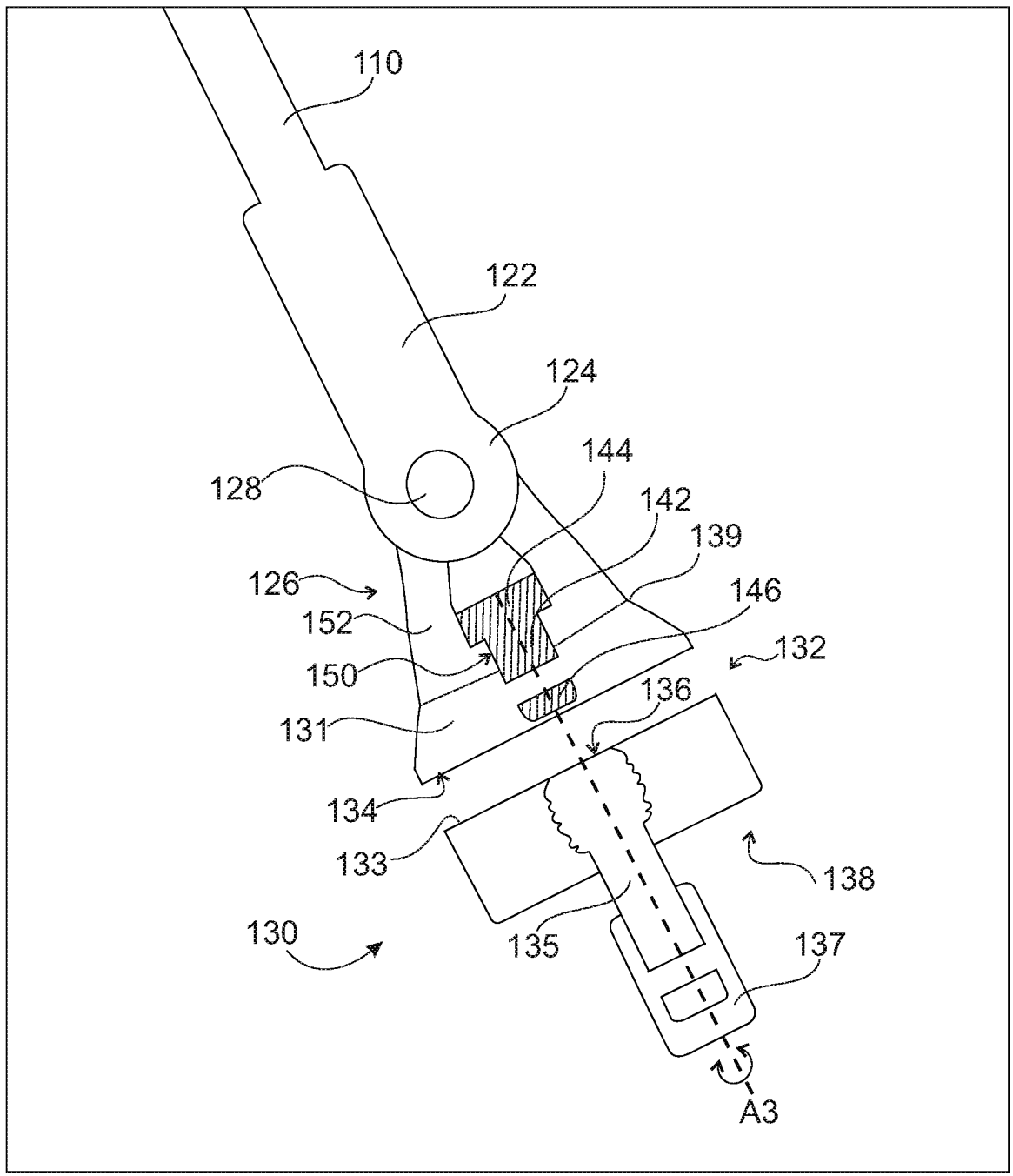
FIG. 9 provides an enlarged view of the swivel clamp portion of the handle adaptor shown in FIG. 8.

While the knob 137 of screw extends beyond the distal end 138 of the clamp body 131, the proximal end 139 of the clamp body 131 is secured to the second leaf 126 of the hinge 120. In this manner, the clamp body 131 may pivot with respect to the extension arm 110 about the axis A2. In order to permit greater flexibility in positioning the retractor 30, 30', the proximal end 139 of the clamp body 131 is secured to the second leaf 126 via a swivel connection 140 as best shown in FIGS. 7-9. The swivel connection 140 includes a pin 142 having a head 144 and distal end 146. The pin 142 passes through a bearing 150 in a base 152 of the second leaf 126 of the hinge 120. The distal end 146 is affixed to the proximal end 139 of the clamp body 131. The head 144 is sized to be greater than opening provided by the bearing 150. As such, the clamp body 131 is secured to the hinge 120, but permitted to swivel about the axis A3 provide by pin 142. In the depicted embodiment, the swivel axis A3 is distinct or at a different orientation than the hinge axis A2 provided by hinge 120. In an embodiment, the swivel axis A3 is perpendicular to the hinge axis A2.

While the foregoing has been described with reference to certain aspects and examples, it will be understood by those skilled in the art that various changes may be made and equivalents may be substituted without departing from the scope of the disclosure. In addition, many modifications may be made to adapt a particular situation or material to the teachings of the disclosure without departing from its scope. Therefore, it is intended that the disclosure not be limited to the particular example(s) disclosed, but that the disclosure will include all examples falling within the scope of the appended claims.

What is claimed is:

1. A handle adaptor for securing a surgical retractor having a retractor blade and a handle longitudinally extending from the retractor blade to a frame of a surgical retraction system, the handle adaptor comprising:
   an extension arm having a proximal end and a distal end;
   a hinge comprising a first portion attached to the distal end of the extension arm and a second portion coupled to the first portion at a pivot, wherein the pivot limits movement of the second portion with respect to the first portion about a single pivot axis;
   a clamp comprising a clamp body that includes a proximal end; and
   a swivel connection that attaches the proximal end of the clamp body to the second portion of the hinge,
   wherein the swivel connection permits rotation of the clamp body with respect to the second portion of the hinge about a single swivel axis that intersects the single pivot axis, wherein the clamp body further includes a distal end opposite the proximal end of the clamp body and one or more sidewalls adjoining the distal end of the clamp body to the proximal end of the clamp body, wherein the clamp body further includes a first slot surface, a second slot surface opposite the first slot surface, and a slot end surface, wherein the first and second slot surfaces each extend from a slot opening in a first sidewall of the one or more sidewalls to the slot end surface to form a slot in the clamp body that is accessible via the slot opening in the first sidewall, and wherein, when the handle is laterally received by the slot via the slot opening, the first slot surface aligns with an upper surface of the handle, and the second slot surface aligns with a lower surface of the handle that is opposite the upper surface.

2. The handle adaptor of claim 1, wherein the pivot of the hinge comprises a pin that couples the first portion of the hinge to the second portion of the hinge and that provides the single pivot axis of the pivot.

3. The handle adaptor of claim 2, wherein:
the swivel connection comprises a swivel pin that passes through the second portion of the hinge and the proximal end of the clamp body;
the swivel pin secures the proximal end of the clamp body to the second portion of the hinge and limits rotation of the proximal end of the clamp body with respect to the second portion of the hinge about the single swivel axis; and
the single swivel axis aligns with a longitudinal axis of the swivel pin and is distinct from the single pivot axis provided by the hinge.

4. The handle adaptor of claim 3, wherein the single swivel axis is perpendicular to the single pivot axis.

5. The handle adaptor of claim 1, wherein:
the clamp further includes a screw having a tip that passes through the distal end of the clamp body, through the first slot surface, and into the slot; and
the tip of the screw engages the upper surface of the handle of the surgical retractor when received by the slot and clamps the handle between the tip and the second slot surface opposite the tip.

6. The handle adaptor of claim 1, wherein the extension arm is rod-shaped and comprises a stop at the proximal end of the extension arm.

7. The handle adaptor of claim 1, wherein the first slot surface and the second slot surface are flat.

8. A surgical retraction system for retracting tissue of a patient, the surgical retraction system comprising:
a frame comprising one or more bars secured to an operating table;
a universal joint coupled to a bar of the one or more bars of the frame;
a surgical retractor comprising a handle and a blade coupled to the handle, wherein the handle comprises an upper surface, a lower surface opposite the upper surface, and one or more side surfaces that adjoin the upper surface to the lower surface, and wherein the upper surface and lower surface extend longitudinally from a proximal end of the blade; and
a handle adaptor that secures the surgical retractor to the frame via the universal joint,
wherein the handle adaptor comprises an extension arm, a hinge, a clamp, and a swivel connection,
wherein the extension arm comprises an elongated member having a proximal end and a distal end, wherein the hinge comprises a first portion attached to the distal end of the extension arm and a second portion coupled to the first portion at a pivot, wherein the pivot limits movement of the second portion with respect to the first portion about a single pivot axis, wherein the elongated member passes through the universal joint such that the proximal end of the elongated member and the distal end of the elongated member extend from opposite sides of the universal joint, wherein the universal joint selectively engages the extension arm and secures the extension arm to the frame when in an engaged position, wherein the clamp comprises a clamp body that includes a proximal end, wherein the swivel connection attaches the proximal end of the clamp body to the distal end of the extension arm via the hinge, wherein the swivel connection permits rotation of the clamp body with respect to the hinge about a single swivel axis that intersects the single pivot axis, wherein the clamp body further includes a distal end opposite the proximal end of the clamp body and one or more sidewalls adjoining the distal end of the clamp body to the proximal end of the clamp body, wherein the clamp body further includes a first slot surface, a second slot surface opposite the first slot surface, and a slot end surface, wherein the first and second slot surfaces each extend from a slot opening in a first sidewall of the one or more sidewalls to the slot end surface to form a slot in the clamp body that is accessible via the slot opening in the first sidewall, and wherein, when the handle is laterally received by the slot via the slot opening, the first slot surface aligns with the upper surface of the handle and the second slot surface aligns with the lower surface of the handle.

9. The surgical retraction system of claim 8, wherein the proximal end of the clamp body is attached to the second portion of the hinge to permit the proximal end of the clamp body to rotate about the single pivot axis with respect to the extension arm.

10. The surgical retraction system of claim 9, wherein:
the swivel connection comprises a swivel pin that passes through the second portion of the hinge and the proximal end of the clamp body;
the swivel pin secures the proximal end of the clamp body to the second portion of the hinge and limits rotation of the proximal end of the clamp body with respect to the second portion of the hinge about the single swivel axis; and
the single swivel axis aligns with the swivel pin and is distinct from the single pivot axis provided by the hinge.

11. The surgical retraction system of claim 10, wherein the single swivel axis is perpendicular to the single pivot axis.

12. The surgical retraction system of claim 8, wherein:
the clamp further includes a screw having a tip that passes through the distal end of the clamp body, through the first slot surface, and into the slot; and
the tip of the screw engages the upper surface of the handle of the surgical retractor when received by the slot and clamps the handle between the tip and the second slot surface opposite the tip.

13. The surgical retraction system of claim 8, wherein:
the extension arm is rod-shaped with a circular cross-section;
the universal joint has a circular cross-section through which the extension arm passes; and
the universal joint permits rotation of the extension arm about a longitudinal axis of the extension arm when the universal joint is disengaged.

14. The surgical retractor system of claim 8, wherein:
the extension arm is rod-shaped with a non-circular cross-section; and
the universal joint permits rotation of the extension arm about a longitudinal axis of the extension arm when the universal joint is disengaged.

15. The surgical retractor system of claim 8, wherein:
the extension arm is rod-shaped and comprises a stop at the proximal end of the extension arm; and
the universal joint permits the extension arm to slide through the universal joint when disengaged to permit retraction of the clamp toward the universal joint until the universal joint encounters the hinge and extraction of the clamp away from the universal joint until the universal joint encounters the stop.

16. A handle adaptor for securing a surgical retractor having a retractor blade and a handle longitudinally extending from the retractor blade to a frame of a surgical retraction system, the handle adaptor comprising:
an extension arm having a proximal end and a distal end;
a hinge attached to the distal end of the extension arm;
a clamp comprising a clamp body that includes a proximal end, wherein the hinge limits movement of the clamp about a single pivot axis of the hinge; and
a swivel pin that passes through the hinge and the proximal end of the clamp body, secures the proximal end of the clamp body to the hinge, and limits rotation of the proximal end of the clamp body with respect to the hinge about a single swivel axis aligned with the swivel pin, wherein the single swivel axis intersects the single pivot axis;
wherein the clamp body further includes a distal end opposite the proximal end of the clamp body and one or more sidewalls adjoining the distal end of the clamp body to the proximal end of the clamp body,
wherein the clamp body further includes a first slot surface, a second slot surface opposite the first slot surface, and a slot end surface,
wherein the first and second slot surfaces each extend from a slot opening in a first sidewall of the one or more sidewalls to the slot end surface to form a slot in the clamp body that is accessible via the slot opening in the first sidewall, and
wherein, when the handle is laterally received by the slot via the slot opening, the first slot surface aligns with an upper surface of the handle, and the second slot surface aligns with a lower surface of the handle that is opposite the upper surface.

17. The handle adaptor of claim 16, wherein the hinge comprises a pin that limits movement of the clamp about the single pivot axis of the hinge.

18. The handle adaptor of claim 17, wherein the single swivel axis is perpendicular to the single pivot axis.

19. The handle adaptor of claim 16, wherein the extension arm is rod-shaped and comprises a stop at the proximal end of the extension arm.

20. The handle adaptor of claim 16, wherein the first slot surface and the second slot surface are flat.

* * * * *